(12) United States Patent
Gheith et al.

(10) Patent No.: US 8,663,690 B2
(45) Date of Patent: Mar. 4, 2014

(54) METHOD FOR NANOENCAPSULATION

(75) Inventors: Muhammed K. Gheith, Houston, TX (US); Yu-Lun Fang, Houston, TX (US); Michael S. Wong, Houston, TX (US)

(73) Assignee: William Marsh Rice University, Houston, TX (US)

( * ) Notice: Subject to any disclaimer, the term of this patent is extended or adjusted under 35 U.S.C. 154(b) by 787 days.

(21) Appl. No.: 12/446,553

(22) PCT Filed: Oct. 31, 2006

(86) PCT No.: PCT/US2006/042354
§ 371 (c)(1),
(2), (4) Date: Apr. 21, 2009

(87) PCT Pub. No.: WO2008/063158
PCT Pub. Date: May 29, 2008

(65) Prior Publication Data
US 2010/0303913 A1    Dec. 2, 2010

(51) Int. Cl.
*A61K 9/14* (2006.01)
*A61J 3/07* (2006.01)
*B01J 13/02* (2006.01)

(52) U.S. Cl.
USPC ............. 424/488; 424/484; 264/4; 264/4.1

(58) Field of Classification Search
USPC ............ 424/400, 488, 484; 514/729, 547; 426/89; 264/4, 4.1
See application file for complete search history.

(56) References Cited

U.S. PATENT DOCUMENTS

| | | |
|---|---|---|
| 2,800,457 A | 7/1957 | Green et al. |
| 3,790,688 A | 2/1974 | Walter, Jr. et al. |
| RE28,779 E | 4/1976 | Katayama et al. |
| 4,016,098 A | 4/1977 | Saeki et al. |
| 4,808,408 A | 2/1989 | Baker et al. |
| 4,908,233 A | 3/1990 | Takizawa et al. |

(Continued)

FOREIGN PATENT DOCUMENTS

| | | |
|---|---|---|
| JP | 573861 A | 1/1982 |
| JP | 5292899 A | 11/1993 |

(Continued)

OTHER PUBLICATIONS

Arshady, Reza, "Microspheres and microcapsules, a survey of manufacturing techniques: part II: coacervation," Mid-Aug. 1990, pp. 905-914, vol. 30, No. 15, Polymer Engineering and Science.

(Continued)

*Primary Examiner* — Blessing M Fubara
(74) *Attorney, Agent, or Firm* — Conley Rose, P.C.; Rodney B. Carroll

(57) ABSTRACT

Methods of nanoencapsulation are described herein. Embodiments of the method utilize the coacervation of a cationic polyelectrolyte with an anionic polyelectrolyte to form a novel capsular matrix. In particular, the novel methods may be used to encapsulate a suspension of a hydrophobic material such as a carotenoid. The disclosed methods do not require lengthy pH adjustments nor do they require the use of any toxic crosslinking agents. In one embodiment, a method of encapsulation comprises dispersing a hydrophobic compound in an organic solvent to form a solution. The method also comprises admixing an anionic polyelectrolyte and a cationic polyelectrolyte with the suspension to form a mixture. In addition, the method comprises quiescently cooling the mixture so as to cause self-crosslinking of a capsular matrix encapsulating the hydrophobic particles.

35 Claims, 6 Drawing Sheets

(56) References Cited

U.S. PATENT DOCUMENTS

| | | | |
|---|---|---|---|
| 5,023,024 | A | 6/1991 | Kyogoku et al. |
| 6,039,901 | A | 3/2000 | Soper et al. |
| 6,325,951 | B1 | 12/2001 | Soper et al. |
| 6,488,870 | B1 | 12/2002 | Chopra et al. |
| 6,492,025 | B1 | 12/2002 | Chopra et al. |
| 6,558,698 | B2 | 5/2003 | Morrison et al. |
| 6,592,916 | B2 | 7/2003 | Soeda et al. |
| 6,663,900 | B2 | 12/2003 | DeFreitas et al. |
| 6,720,008 | B2 | 4/2004 | Allison |
| 6,953,593 | B2 * | 10/2005 | Kuhrts ................... 424/490 |
| 6,969,530 | B1 | 11/2005 | Curtis et al. |
| 6,974,592 | B2 | 12/2005 | Yan |
| 7,473,467 | B2 | 1/2009 | Subramaniam et al. |
| 2004/0032036 | A1 | 2/2004 | Subramaniam et al. |
| 2005/0170005 | A1 * | 8/2005 | Rashba-Step et al. ........ 424/490 |
| 2006/0165990 | A1 * | 7/2006 | Curtis et al. ............... 428/402.2 |

FOREIGN PATENT DOCUMENTS

| | | |
|---|---|---|
| WO | 9620612 A1 | 7/1996 |
| WO | 2004022220 A1 | 3/2004 |
| WO | 2006023207 A2 | 3/2006 |
| WO | 2006023207 A3 | 3/2006 |
| WO | WO 2006/023207 A2 * | 3/2006 |
| WO | 2008063158 A2 | 5/2008 |
| WO | 2008063158 A3 | 5/2008 |

OTHER PUBLICATIONS

Author unknown, "Carotenoid," http://en.wikipedia.org/wiki/Carotenoids, Sep. 12, 2006, 2 pages, Wikipedia, the free encyclopedia.

Author unknown, "Coacervation," http://www.pharmarom.de/en/tech/koazervation.html, Sep. 12, 2006, 1 page, PHARMAROM.

Deasy, Patrick B., "Microencapsulation and related drug processes," 1984, 1 cover page, 1 title page, and 1 publishing page, Marcel Dekker, Inc., New York.

Foreign communication from the priority application—International Preliminary Report on Patentability, PCT/US2006/042354, May 5, 2009, 6 pages.

Foreign communication from the priority application—International Search Report and Written Opinion, PCT/US06/42354, Jun. 13, 2008, 6 pages.

Gibbs, Bernard F., et al., "Encapsulation in the food industry: a review," International Journal of Food Sciences and Nutrition, 1999, pp. 213-224, vol. 50, Taylor & Francis Ltd.

Gouin, Sébastien, "Micro-encapsulation: industrial appraisal of existing technologies and trends," Trends in Food Science & Technology, 2004, pp. 330-347, vol. 15, Elsevier Ltd.

Granado, F., et al., "Nutritional and clinical relevance of lutein in human health," British Journal of Nutrition, 2003, pp. 487-502, vol. 90, The Authors.

Author unknown, "Gum arabic," http://www.lsbu.ac.uk/water/hyarabic.html, Sep. 12, 2006, 2 pages.

Horn, Dieter, et al., "Organic nanoparticles in the aqueous phase—theory, experiment, and use," Angew. Chem. Int. Ed., 2001, pp. 4331-4361 plus 1 cover page, vol. 40, WILEY-VCH Verlag GmbH, D-69451, Weinheim.

Horn, Dieter, "Preparation and characterization of microdisperse bioavailable carotenoid hydrosols," Die Angewandte Makromolekulare Chemie, 1989, pp. 139-153, vol. 166/167, Hüthig & Wepf Verlag, Basel.

Hunkeler, David, et al., "Particle coating: nutraceuticals and probiotics," Jun. 26-28, 2002, pp. 1-5, Glatt TTC Workshop, Binzen, Germany.

Ichwan, Andreas M., et al., "Use of gelatin—acacia coacervate containing benzocaine in topical formulations," Journal of Pharmaceutical Sciences, Aug. 1999, pp. 763-766, vol. 88, No. 8, American Chemical Society and American Pharmaceutical Association.

Ijichi, Kazuya, et al., "Multi-layered gelatin/acacia microcapsules by complex coacervation method," 1997, pp. 793-798, vol. 30, No. 5, Journal of Chemical Engineering of Japan.

Jizomoto, Hiroaki, "Phase separation induced in gelatin-base coacervation systems by addition of water-soluble nonionic polymers I: microencapsulation," Journal of Pharmaceutical Sciences, Jul. 1984, pp. 879-882, vol. 73, No. 7, American Pharmaceutical Association.

Luzzi, Louis A., et al., "Effects of selected variables on the extractability of oils from coacervate capsules," Apr. 1964, pp. 429-431 vol. 53, No. 4, Journal of Pharmaceutical Sciences.

Mayya, KS, et al., "Micro-encapsulation by complex coacervation: influence of surfactant," Polymer International, 2003, pp. 644-647, vol. 52, Society of Chemical Industry.

Osman, Mohamed E., et al., "Characterization of commercial samples of gum arabic," J. Agric. Food Chem., 1993, pp. 71-77, vol. 41, No. 1, American Chemical Society.

Phillips, G. O., et al., Editors, "Handbook of hydrocolloids," 2000, 1 cover page, 1 title page, and 1 publishing page, Woodhead Publishing Limited, England, Published in North and South America by CRC Press LLC, United States, © by Woodhead Publishing Limited.

Rabišková, M., et al., "The influence of HLB on the encapsulation of oils by complex coacervation," J. Microencapsulation, 1998, pp. 747-751, vol. 15, No. 6, Taylor & Francis Ltd.

Author unknown, "Structures of carotenoids," http://www.carotenoidsociety.org/carotenoids/carotenoids2.html., Sep. 12, 2006, 1 page, Carotenoid Society.

Yeo, Yoon, et al., "Complex coacervates for thermally sensitive controlled release of flavor compounds," Journal of Agricultural and Food Chemistry, 2005, pp. 7518-7525, vol. 53, No. 19, American Chemical Society.

* cited by examiner

METHOD FOR NANOENCAPSULATION

CROSS-REFERENCE TO RELATED APPLICATIONS

This application is a filing under 35 U.S.C. 371 of International Application No. PCT/US2006/042354 filed Oct. 31, 2006, entitled "Method for Nanoencapsulation," which application is incorporated by reference herein in its entirety.

TECHNICAL FIELD OF THE INVENTION

This invention relates generally to the field of nanoencapsulation. More specifically, the invention relates to a novel method of modified coacervation.

BACKGROUND

The term encapsulation refers to the formation of a matrix surrounding a solid, liquid, or gaseous material. The encapsulation process is often used to turn sensitive, reactive, or unstable substances into protected and easily administered compounds. In the food and pharmaceutical industries, encapsulation of food ingredients is used for a number of applications including coating, smell or taste masking, increasing shelf life, improved processing, protecting sensitive materials, and delivering specific doses. Coacervation is the most commonly used method of encapsulation due to its high encapsulation yield and its controlled release capability. In general, coacervation refers to the formation of phase separated aggregates and the subsequent adsorption of the aggregates around a core material. Coacervation may be either complex (i.e. using two oppositely charged polyelectrolytes) or simple (i.e. using a single polyelectrolyte).

The most extensively used positive polyelectrolyte in coacervation is gelatin, a protein derived from collagen. The most often used negatively-charged polyelectrolyte in combination with gelatin is gum arabic, a polysaccharide exuded from acacia trees. Complex coacervation of gelatin and gum arabic has been widely used because both compounds are non-toxic, natural, and biodegradable.

Generally, current state-of-the-art coacervation processes using gelatin and gum arabic include the following four steps: emulsification, coacervation, wall formation, and wall hardening. Typically, the process begins by mixing gelatin and the gum arabic, and adjusting the pH of the mixture. The core material is then emulsified in the mixture, followed by another pH adjustment which causes the gelatin and gum arabic to coacervate. The coacervate mixture is then cooled to induce wall formation of the microcapsules. Finally, a hardening or a crosslinking agent such as glutaraldehyde is added to the microcapsules to harden the capsules wall.

There are several disadvantages associated with current coacervation processes. For example, gelatin-gum arabic coacervation requires several pH adjustment and dehydration steps. Furthermore, a toxic crosslinking agent such as glutaraldehyde or formaldehyde is usually needed to complete hardening of the microcapsule walls. Such toxic compounds are undesirable for use in the food industry.

Consequently, there is a need for a simple encapsulation method without the use of toxic compounds.

SUMMARY OF THE INVENTION

Methods of nanoencapsulation are described herein. Embodiments of the method utilize the self-crosslinking of a cationic polyelectrolyte with an anionic polyelectrolyte to form a novel capsular matrix. In particular, the novel methods may be used to encapsulate a suspension of a hydrophobic material such as a carotenoid. The disclosed methods do not require lengthy pH adjustments nor do they require the use of any toxic crosslinking agents.

These and other needs in the art are addressed in one embodiment via a method of encapsulation comprising admixing a hydrophobic compound in an organic solvent to form a mixture. The method also comprises admixing an anionic polyelectrolyte and a cationic polyelectrolyte with the mixture to form a suspension of encapsulated hydrophobic particles. In addition, the method comprises quiescently cooling the suspension so as to cause self-crosslinking of the encapsulated hydrophobic particles to form a capsular matrix.

In an embodiment, a capsular matrix comprises a self-crosslinked network of capsules encapsulating a plurality of hydrophobic particles. Each capsule comprises a cationic polyelectrolyte and an anionic polyelectrolyte.

Compared to prior art methods of encapsulation, the disclosed method yields nanocapsules and mesocapsules in a simple, fast, and non-expensive way. As defined herein, nanocapsules are capsules with an average diameter ranging from about 1 nm to about 100 nm. Mesocapsules are capsules with an average diameter ranging from about 100 nm to about 1 µm. The small size of the resultant capsules improves the solubility of the capsules in water and increases the capsules bioavailability. Hybrid structures of anionic polyelectrolytes and cationic polyelectrolytes form a coating around the hydrophobic particles that shield them from exposure to light, heat, and oxygen that could degrade the particles. No pH adjustment is necessary to form the capsules and no additional hardening materials or structuring agents are needed. This reduces the preparation cost and eliminates any toxicity concerns, which makes the disclosed methods useful for the food and pharmaceutical industries. The formation of capsules into a matrix configuration also offers easy and fast processing into a powder that can be easily dissolved in water to form suspensions or can be pressed into tablets.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims, to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

Figure 1:
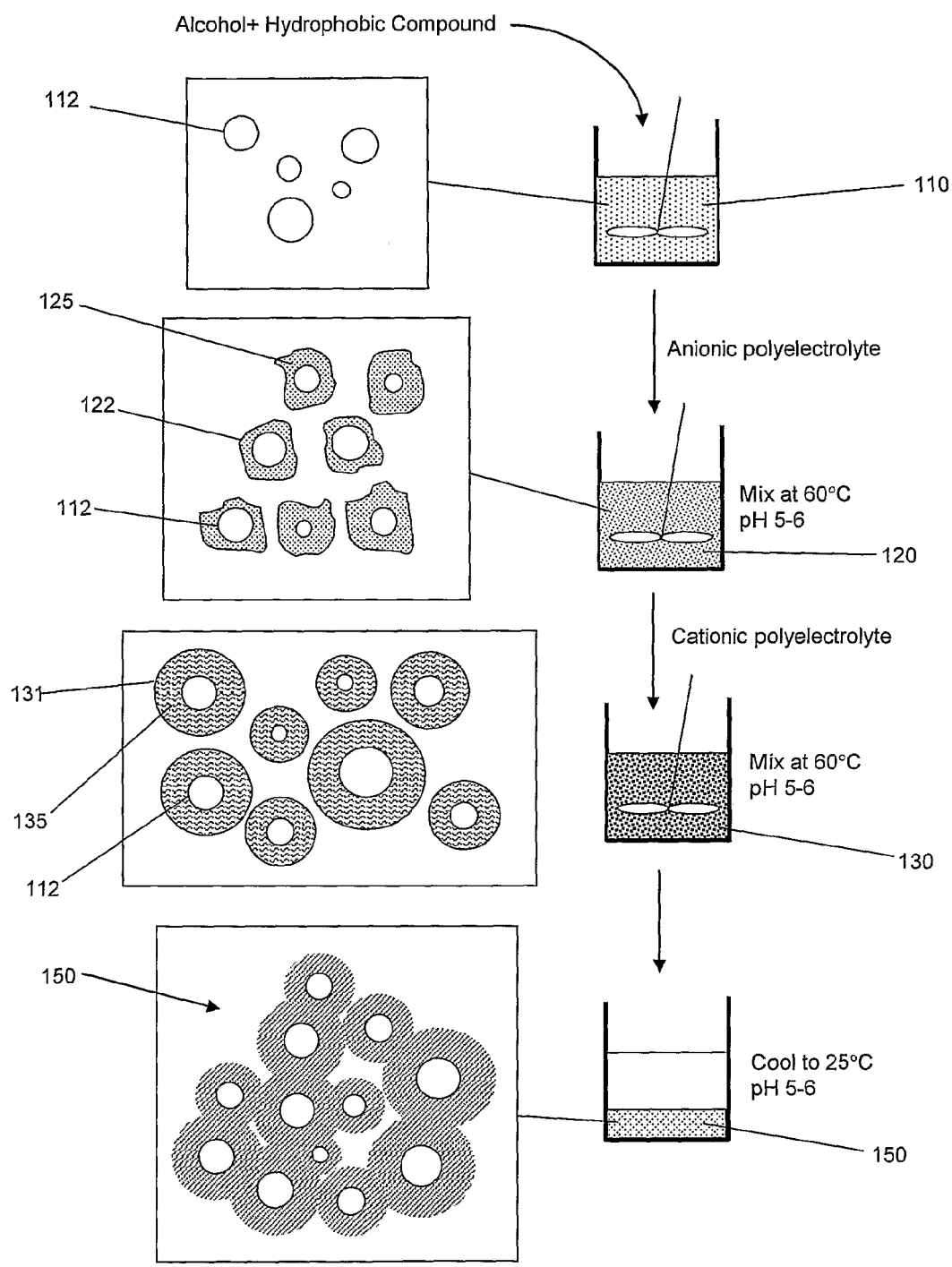
FIG. 1 illustrates an embodiment of method for nanoencapsulation.

FIG. 1 illustrates an embodiment of a method of encapsulation. In an embodiment, a hydrophobic compound is first admixed in an organic solvent to form a mixture 110. To form the mixture, an amount of a hydrophobic compound is dissolved in the organic solvent by heating and mixing. In embodiments where the hydrophobic compound is an oil, the oil may be suspended in water to form small emulsion droplets suspended in water. Preferably, the mixture 110 is a solution composed of dissolved molecules of the hydrophobic compound. In some embodiments, the concentration of hydrophobic compound in the organic solvent exceeds the saturation point of the solvent. Accordingly, a portion of the hydrophobic compound may remain undissolved and suspended in the solvent. In other words, the mixture of the hydrophobic compound and the organic solvent forms a partial solution of the hydrophobic compound. Thus, in some embodiments, the mixture 110 may be composed of a suspension of solid particles 112 including nanoparticles (<100 nm), mesoparticles (100-1000 nm), and microparticles (>1000 nm) of the hydrophobic compounds that are not dissolved in the organic solvent as well as a solution of the hydrophobic compound. However, mixture 110 may also comprise an emulsion, a suspension or other type of solution depending on the hydrophobic compound and solvent selected.

Particles, as defined herein, are either solid particulate matter or droplets of hydrophobic liquid. The hydrophobic compound and solvent may be heated to any suitable temperature. Generally, however, the hydrophobic compound and solvent are heated to a temperature in a range preferably from 40° C. to about 80° C., more preferably from about 40° C. to about 60° C. In various embodiments, the concentration of hydrophobic compound in the suspensions ranges from about 0.5 wt % to about 5.0 wt %, preferably from about 0.75 wt % to about 3.0 wt %, more preferably from about 1.0 wt % to about 2.0 wt %.

The solvent may be any solvent known to those of skill in the art. In a preferred embodiment, the organic solvent comprises an alcohol. Examples of suitable alcohols include without limitation, ethanol, methanol, propanol, hexanol, acetone and combinations thereof. In particular embodiments, the alcohol is at a concentration in the solvent ranging from about 90 wt % to about 99 wt % alcohol, preferably from about 95 wt % to about 99 wt % alcohol, more preferably from about 97 wt % to about 99 wt % alcohol.

Generally, the hydrophobic compound may comprise any water-insoluble material in solid powder form. In a specific embodiment, the hydrophobic compound is a carotenoid. Carotenoids are organic pigments naturally occurring in plants and some other photosynthetic organisms. In a preferred embodiment, the carotenoid is lutein. However, the carotenoid may be any suitable carotenoid. Examples of suitable carotenoids include without limitation, antheraxanthin, astaxanthin, canthaxanthin, alpha-carotene, beta-carotene, gamma-carotene, cryptoxanthin, diatoxanthin, fucoxanthin, fucoxanthinol, lactucaxanthin, lycopene, neoxanthin, neurosporene, peridinin, phytoene, rhodopin, siphonaxanthin, spheroidene, spirilloxanthin, uriolide, uriolide acetate, violaxanthin, zeaxanthin, or combinations thereof. The embodiment also includes the encapsulation of other hydrophobic substances, including without limitation, coenzymes Q and phytosterols. Co-enzymes Q are organic pigments naturally existing in every plant and animal cell. In a preferred embodiment, the co-enzyme Q is co-enzyme Q-10. Phytosterols are pigments naturally existing in plants and are chemically similar to cholesterol. In a preferred embodiment, the phytosterol is beta-sitosterol.

In another embodiment, the hydrophobic compound is a liquid. The hydrophobic compound may comprise a biocompatible oil. Examples of such oils include without limitation, olive oil, vegetable oil, animal fat, soybean oil, peanut oil, flaxseed oil, canola oil, mineral oil, fish oil, rapeseed oil, sunflower oil, corn oil, cottonseed oil, coconut oil, palm oil, or combinations thereof. In other embodiments, the hydrophobic compound is a fatty acid such as without limitation, butyric acid, stearic acid, palmitic acid, myristic acid, arachidic acid, an unsaturated fatty acid, or combinations thereof.

In a further embodiment, an anionic polyelectrolyte is added to the mixture to form a suspension 120 of hydrophobic particles 112 encapsulated by the anionic polyelectrolyte 125. In one embodiment, the anionic polyelectrolyte is first dissolved in water to form an anionic polyelectrolyte solution and then admixed with the mixture 110. The anionic polyelectrolyte is generally dissolved in a liquid such as water at a concentration ranging from 0.1 wt % to about 10.0 wt %, preferably from about 0.25 wt % to about 5.0 wt %, more preferably from about 0.5 wt % to about 3.0 wt %. Alternatively, the anionic polyelectrolyte may be added directly to the mixture. Typically, the anionic polyelectrolyte is added to the mixture 110 as it is being stirred at room temperature. In addition, the anionic polyelectrolyte may be added to the carotenoid mixture at elevated temperatures. For example, the suspension 120 may be heated to a temperature of 60° C., preferably 70° C., more preferably 80° C. The anionic polyelectrolyte preferably comprises gum arabic. Alternatively, the anionic polyelectrolyte may comprise other compounds such as, without limitation, any anionic polysaccharide, alginate, pectin, agar, carrageenan, or combinations thereof.

In an embodiment, a cationic polyelectrolyte is admixed with the suspension 120 to form a second suspension 130 as shown in FIG. 1. Second suspension 130 comprises hydrophobic particles 112 encapsulated by a shell 135 of the anionic and cationic polyelectrolyte. Preferably, the cationic polyelectrolyte is admixed with the mixture under rigorous stirring conditions. In general, the cationic polyelectrolyte is added to the suspension 120 as a cationic polyelectrolyte solution. The cationic polyelectrolyte in the cationic polyelectrolyte solution is at a concentration in a range of about 0.1 wt % to about 10 wt %, preferably in the range of about 0.25 wt % to about 5 wt %, more preferably in the range of about 0.5 wt % to about 3 wt %. According to at least one embodiment, the amount of cation polyelectrolyte added to the suspension 120 is at least twice the amount of anionic polyelectrolyte present in the suspension 120. In an embodiment, once the cationic polyelectrolyte is added to form a second suspension 130, second suspension 130 is mixed for a period of time ranging from 1 minute to 30 minutes. In particular embodiments, second suspension 130 is stirred at a speed ranging from about 500 rpm to about 4000 rpm.

The cationic polyelectrolyte is preferably gelatin such as gelatin A or gelatin B. The gelatin may comprise any suitable bloom strength. As defined herein, bloom strength of gelatin is a measure of the gelation strength of gelatin (usually a measure of the weight in grams needed by a probe to deflect the surface of the gel without breaking it). However, the cationic polyelectrolyte may comprise any suitable material. Examples of other suitable cationic polyelectrolytes include without limitation, chitosan, whey protein, albumin, beta-lactoglobulin, potato protein, faba bean legumin, soybean protein, or combinations thereof.

In alternative embodiments, the order at which the anionic polyelectrolyte and the cationic polyelectrolyte are added is switched. That is, the cationic polyelectrolyte may be added to the mixture 110 first, followed by addition of the anionic polyelectrolyte. Furthermore, it is contemplated that the anionic polyelectrolyte and cationic polyelectrolyte may be added simultaneously to the mixture 110 to form the suspension 130. In addition, in embodiments where the hydrophobic compound is an oil, the hydrophobic compound, the anionic polyelectrolyte and cationic polyelectrolyte may be mixed simultaneously to form the suspension 130. Thus, the order of anionic polyelectrolyte or cationic polyelectrolyte has no effect on the formation of the capsular matrix described below.

Referring still to FIG. 1, the encapsulation of the hydrophobic compound is based on the ability to form a polymeric layer around the surface of the hydrophobic particles 112. In at least one embodiment, under heating and mixing, admixing the hydrophobic compound in the organic solvent leads to complete dissolution of the hydrophobic compound into dissolved molecules. In another embodiment, an amount of hydrophobic compound is admixed with the organic solvent at a concentration greater than the saturation point of the organic solvent resulting in only partial dissolution of the hydrophobic compound. The remaining undissolved material forms nanoparticles and mesoparticles of the hydrophobic compound.

Because of the hydrophobic nature of the compound, the addition of water to the mixture 110 typically causes the dissolved molecules of the hydrophobic compound to precipitate and adhere together to form nanoparticles or mesoparticles. Addition of water may also cause the undissolved hydrophobic particles to form larger aggregates. Without being limited by theory, it is believed that the anionic polyelectrolyte in the water solution coats the particles to form a polymer shell 125, which reduces the tendency for particle aggregation and macroscopic precipitation of a powder. As such, the polymer shell helps keep the particle sizes small. The anionic polyelectrolyte molecules stabilize the existing nanoparticles and mesoparticles 112 of the hydrophobic compound by forming nano-sized to meso-sized entities 122 where the hydrophobic particles 112 are shielded from the aqueous medium by the negatively-charged anionic polyelectrolyte coating 125. Upon adding the cationic polyelectrolyte, the anionic polymer shell interacts electrostatically with the positively-charged cationic polyelectrolyte molecules. This yields the formation of nano-sized to meso-sized capsules 131 in which the hydrophobic particles 112 are coated with a polymer shell 135 of anionic polyelectroyte and cationic polyelectrolyte hybrid structures.

The order at which the coating polymers are added to the initial mixture has no effect on the resulting nanoencapsulation (see Example 3 below). Cationic polyelectrolyte molecules are also believed to stabilize the hydrophobic particles 112 in the same way the anionic polyelectrolyte does by forming a coating shield around the hydrophobic particles 112. When an anionic polyelectrolyte solution is added to the suspension, the cationic structures interact with anionic molecules to induce hybrid structures that form the wall 135 of the capsules. These hybrid structures are also believed to form around the hydrophobic particles when both anionic polyelectrolyte and cationic polyelectrolyte solutions are added simultaneously.

Second suspension 130, once formed, is cooled to a temperature ranging from about 20° C. to about 30° C. (i.e. room temperature) to form a capsular matrix 150. In an embodiment, the mixture is allowed to cool quiescently (or without stirring) at room temperature for a time period ranging from about 30 minutes to about 24 hours, preferably from about 1 hour to about 12 hours. Without being limited by theory, it is believed that cooling causes the capsules to precipitate from solution and interact with each other to form the capsular network or matrix 150. More specifically, the excessive amount of cationic polyelectrolyte is believed to be one factor in inducing the formation of the capsular network. Not being bound by theory, it is theorized that upon cooling the suspension, the excessive cationic polyelectrolyte molecules may deposit on the surface of the formed capsules and participate as cross-linkers between the capsules. The joined capsules precipitate out and self-assemble to form a network of cross-linked capsules. Generally, the network of cross-linked capsules resembles a paste.

The pH of the mixture during cooling is in the range of about 5 to about 6, which is the ambient pH of water. An aspect of the disclosed method is that the pH throughout the disclosed method is generally constant. In other words, there is typically no need to alter or adjust the pH of any of the solutions at any time to induce coacervation as required by other methods. However, in some embodiments, it is envisioned that the pH of the mixture may be adjusted if necessary to facilitate the coacervation.

Once the capsular network 150 has been formed from the suspension, the remaining liquid may be removed by decanting or other appropriate method. The capsular matrix is typically spongy, pasty, or cake-like in texture. The capsular matrix 150, once formed, may be dissolved in water at a temperature ranging from about 40° C. to 60° C. to form a suspension of nanocapsules or mesocapsules. In embodiments, the nanocapsules have an average diameter ranging from about 1 nm to about 100 nm, whereas the mesocapsules have a diameter ranging from about 100 nm to about 1000 nm.

Figure 3:
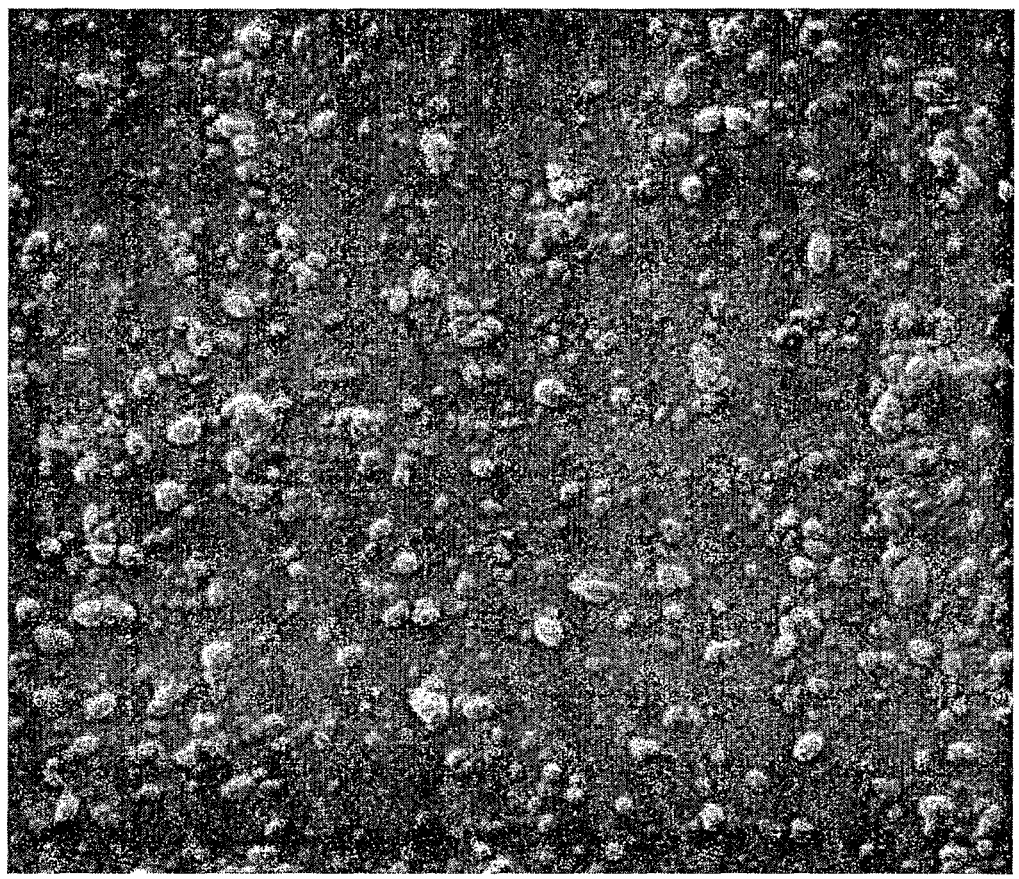
FIG. 3 is a scanning electron micrograph of particles after dissolving the capsular matrix in water.

It is emphasized that the capsular matrix is not an agglomeration of capsules, but a network of capsules that are bonded or crosslinked to each other. As defined herein, crosslinking refers to non-covalent bonding between capsules. Self-crosslinking means crosslinking between capsules without the use of an external crosslinking compound. In other words, the network of capsules may be bonded to each other through hydrophobic interactions or other non-covalent mechanisms. As seen in FIG. 3, when placed in water at elevated temperatures, the capsular matrix forms a suspension of individual nanoscale or mesoscale unagglomerated capsules. Without being limited by theory, if the capsular matrix was merely an agglomeration of capsules, the agglomerations would be insoluble in the water and thus, incapable of forming a suspension.

In certain embodiments, a binder is added to the capsular network, causing the capsular network to dissolve. The binder may comprise any suitable compound such as a salt. Examples of suitable binders include without limitation, $CaCl_2$, $CaCO_3$, $NaHCO_3$, NaCl, $Na_2SO_4$, $MgSO_4$, corn starch, colloidal silica, or combinations thereof. The capsular network in combination with the binder is ground up to form a dry powder. Without being limited by theory, it is believed that the binder forms a coating layer around the capsules. The capsular powder may be re-suspended in any liquid to form a suspension. Alternatively, the capsular powder may be pressed into tablet form.

It is envisioned that the novel capsular powders formed by embodiments of the method may have numerous applications. For example, capsules formed by embodiments of the method can be used to encapsulate a variety of materials for use in the food industry including: food nutrition and dietary supplements, food additives, food flavors, oils, vitamins, etc. Additionally, embodiments of the method may be used to encapsulate pharmaceuticals, drugs, cosmetic products, or, surfactants. Dyes and colors may be encapsulated for printing applications. Nanomaterials including gold and silver metallic nanoparticles, iron oxide magnetic nanoparticles, and cadmium-selenide, -sulfide and -telluride quantum dots may be encapsulated using the novel capsular matrix in cancer therapies or drug delivery applications.

To further illustrate various illustrative embodiments of the present invention, the following examples are provided.

EXAMPLE 1

Paste Preparation of Lutein-ester Capsules

Lutein is one of the six hundred known naturally existing carotenoids. It can be extracted from marigold flower in the form of lutein-ester ($C_{72}H_{116}O_4$, MW 1045.71). Upon uptake by the body, lutein-ester gets converted to free lutein that is then transferred to the macula lutea of the retina where it densely accumulates. Because of the marked antioxidant activity of lutein, it can prevent light-initiated oxidative damage to the retina and therefore, can prevent Age-related Macular Degeneration (AMD) [Granado F., "Nutritional and Clinical Relevance of Lutein in Human Health," British J. Nutr., vol. 90, pp 487-502, 2003]. Lutein is part of the human diet when green leafy vegetables are consumed. However, the natural amounts of lutein tend to decline in the body with age. Thus, fortification of lutein as a dietary supplement could restore the natural balance of processing for many applications in both food and pharmaceutical industries. In addition, the high sensitivity of lutein to light, oxygen and moisture has hampered its activity to be utilized in many applications. Therefore, encapsulating this compound may preserve the stability and functionality of lutein and render it water-soluble.

In this example, we demonstrate the use of the present method to prepare a matrix of encapsulated lutein-ester that contains % 2.0 by weight lutein-ester and % 98.0 by weight gum arabic, gelatin A and water. A suspension of lutein-ester (Blue California, Co.) was prepared by dissolving lutein-ester powder in ethanol at 60° C. under stirring. It is estimated from UV-vis spectroscopy that 20.0 wt % lutein-ester dissolves in ethanol at 60° C., and the rest are in the form of undissolved nanoparticles, mesoparticles, and microparticles. A solution of gum arabic (Sigma) was prepared by dissolving gum arabic in deionized water (18.2 Mega-Ohm·cm) at 60° C. under stirring until the gum arabic was completely dissolved and a clear solution was obtained.

Figure 2:
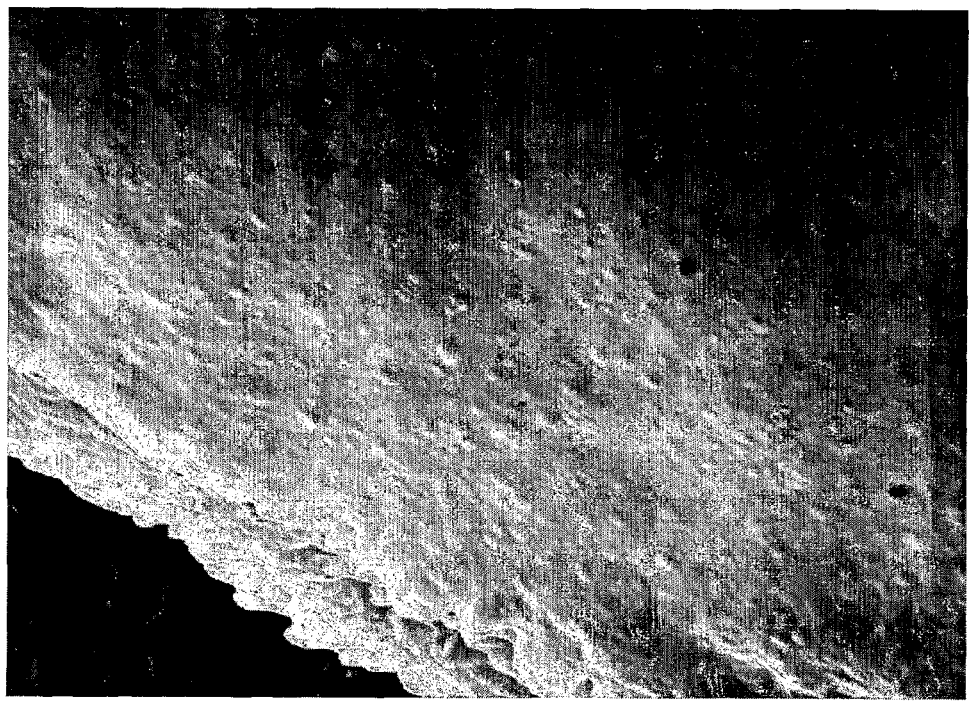
FIG. 2 is a scanning electron micrograph of the capsular matrix.

The gum solution was then added quickly to the lutein-ester/ethanol mixture at 60° C. under rigorous stirring. A solution of gelatin A (300 bloom strength, Sigma) was prepared by dissolving gelatin A in deionized water. The gelatin solution was heated at 60° C. until a clear transparent solution of gelatin was obtained. After 5-min of mixing the lutein-gum mixture, the gelatin A solution was added to the mixture at 60° C. under rigorous stirring and the entire mixture was left to stir for 5-min. The resulting orange solution was then left to cool at room temperature. Upon cooling, the formed (gum/gelatin)-coated lutein-ester nano-and meso-capsules were seen to precipitate at the bottom of the used glass vial to finally form the lutein capsular matrix. The supernatant was discarded and the paste was rinsed multiple times with deionized water to remove any residual ethanol. FIG. 2 illustrates an image of the resulting paste of lutein-ester nano- and meso-capsules. The paste is a capsular matrix composed of gum arabic/gelatin-coated lutein-ester nano- and meso-capsules that are crosslinked in a network structure as shown by the scanning electron micrograph in FIG. 2.

EXAMPLE 2

Suspension Preparation Using Lutein Capsular Matrix

Figure 4:
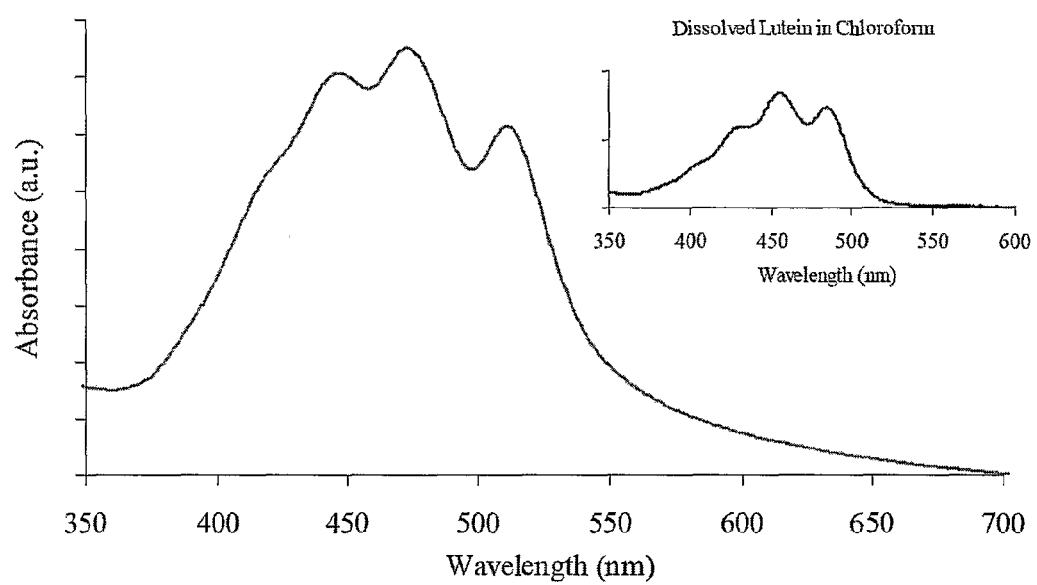
FIG. 4 is an ultra-violet/visible absorption spectra of the nano-and meso-capsules after dissolving the capsular matrix in water.

A suspension of lutein-ester nano-and meso-capsules was prepared by heating 1 g of lutein capsular matrix produced according to example 1 in 10 ml deionized water at 40° C. FIG. 3 shows a scanning electron micrograph of lutein nano- and meso-capsules after dissolving the lutein capsular matrix. This figure shows that the resultant capsules have a size in the 90-1000 nm range. In addition to the nano-and meso-capsules, there may be particles that contain little to no lutein. Any un-encapsulated lutein-ester was extracted from the capsules suspension by adding chloroform to the suspension. Chloroform readily dissolves lutein-ester and is not miscible with water. FIG. 4 illustrates a UV-Vis absorption spectrum of lutein-ester capsules/water suspension verifying the presence of lutein-ester in the capsules. Lutein-ester dissolved in chloroform exhibited the UV-Vis spectrum shown in FIG. 4 inset.

EXAMPLE 3

Lutein-ester Capsular Matrix Preparation with the Order of Adding Gum Arabic and Gelatin Polyelectrolytes Reversed In this example, a lutein-ester capsular matrix was produced in the same manner as in example 1, except that gelatin A solution was added first to the lutein/ethanol mixture and rigorously stirred for 5-min at 60° C. The gum arabic solution was then added to the lutein-gelatin mixture and the entire mixture was left to stir for 5-min at 60° C. The resulting orange solution was then left to cool at room temperature. The resultant lutein-ester capsular matrix resembled the one produced according to example 1.

EXAMPLE 4

Lutein-ester Capsular Matrix Preparation with Gum Arabic and Gelatin Polyelectrolytes Added Simultaneously In this example, a lutein-ester capsular matrix was produced in the same way as in example 1, except that both gum arabic and gelatin A solutions were added simultaneously to the lutein-ester/ethanol mixture under rigorous stirring at 60° C. The mixture was stirred for 5-min and then cooled at room temperature. The resultant lutein-ester capsular matrix was similar to that produced according to example 1.

In all the previous examples, the concentration of gelatin in the suspension was twice as much as that of gum arabic. The presence of excessive amount of gum Arabic, as compared to gelatin amount, did not yield the formation of lutein capsular matrix. Additionally, no lutein capsular matrix was formed when the same amount of gelatin and gum arabic polymers were added to the encapsulating mixture. Instead, a suspension of lutein-ester capsules coated with a layer of gum arabic/gelatin hybrid structures was obtained. The size of these lutein capsules was in the same nano-scale (i.e., 1-100 nm) to meso-scale range (i.e., 100-1000 nm) as that of the capsules contained in the capsular matrix.

EXAMPLE 5

Preparation of Lutein-ester capsular Matrix Using Gelatin B

This example demonstrates the possible use of gelatin B (derived from bovine skin) as an alternative to gelatin A (which is derived from pig skin). A lutein-ester capsular matrix that contains % 1.0 by weight lutein-ester and % 99.0 by weight gum arabic, gelatin B, and water was prepared. A suspension of lutein-ester (Blue California, Co.) was prepared by dissolving lutein-ester powder in ethanol at 60° C. under stirring. A solution of gum arabic (Sigma) was prepared by dissolving gum arabic in deionized water (18.2 Mega-Ohm·cm) at 60° C. under stirring until the gum arabic was completely dissolved and a clear solution was obtained. The gum solution was then added quickly to the lutein-ester/ethanol mixture at 60° C. under rigorous stirring. A solution of gelatin B (225 bloom, Sigma) was prepared by dissolving gelatin B in deionized water. The gelatin solution was heated at 60° C. until a clear transparent solution of gelatin was obtained and the pH was adjusted to pH 3.0 using HCl (1 M). After 5-min of mixing the lutein-gum mixture, gelatin B solution was added to the mixture at 60° C. under rigorous stirring and the mixture was left to stir for 5-min. The resulting orange solution was then left to cool at room temperature. Upon cooling, the formed (gum/gelatin B)-coated lutein-ester nano-and meso-capsules were seen to precipitate at the bottom of the used glass vial to finally form a lutein-ester capsular matrix. The supernatant was discarded and the paste was rinsed multiple times with deionized water to remove any residual ethanol. The resultant capsular matrix material resembled the capsular matrix material discussed in example 1.

EXAMPLE 6

Suspension Preparation Using Lutein Capsular Matrix Prepared with Gelatin B

A suspension of lutein-ester nano-and meso-capsules was successfully prepared by dissolving 1 g of the lutein capsular matrix produced according to example 5 in 10 ml deionized water at 40° C. The resulting suspension was similar to that discussed in example 2.

EXAMPLE 7

Capsular Matrix Preparation of Extra-virgin Olive Oil Capsules

Two milliliters of extra-virgin olive oil was added in a glass vial and then the hydrophobic nile red dye ($C_{20}H_{18}N_2O_2$, MW 318.37) was added to the oil to a final dye concentration of % 0.003 by weight. The dye was used to enhance the detection of the encapsulated olive oil. A solution of gum arabic (Sigma) was prepared by dissolving gum arabic in deionized water (18.2 Mega-Ohm·cm) at 60° C. under stirring until the gum arabic was completely dissolved and a clear solution was obtained. The gum arabic solution was then added to olive oil under rigorous stirring at 60° C. A solution of gelatin A (300 bloom strength, Sigma) was prepared by dissolving gelatin A in deionized water. The gelatin solution was heated at 60° C. until a clear transparent solution of gelatin was obtained. After 15-min of stirring the olive oil-gum mixture, gelatin A solution was added and the entire mixture was rigorously stirred for an additional 15-min at 60° C. The sample was then left to cool at room temperature. After the sample had cooled down, a capsular matrix of olive oil was seen to form at the bottom of the vial.

EXAMPLE 8

Suspension Preparation Using Olive Oil Capsular Matrix

The olive oil capsular matrix formed according to example 7 was rinsed with deionized water multiple times and then dissolved by adding 5 ml of deionized water at 40° C. Optical microscopy showed the presence of 1 to 50 microns size spherical capsules of olive oil that are believed to be coated with a shell of gum arabic and gelatin hybrid structures. Red fluorescence from the nile red dye encapsulated with olive oil helped verify the formation of the capsules and indicated that the formed olive oil capsular matrix is composed of olive oil capsules. This result indicated that the current method can also be used to encapsulate oils.

EXAMPLE 9

Friable Powder Preparation Using Lutein-ester Capsular Matrix and Calcium Chloride (Lutein-ester Powder Preparation Using $CaCl_2$)

Five grams of calcium chloride dihydrate ($CaCl_2.2H_2O$) was added to 1 g of lutein-ester capsular matrix prepared according to example 1 and was grounded to yield lutein-ester powder. The resulting powder contained less than 1 percent by weight lutein-ester. Because of the hygroscopic nature of calcium chloride and its useful property as a drying material, the addition of excessive amounts of $CaCl_2$ to lutein-ester capsular matrix causes the capsular matrix to dissolve. Under continuous mixing and grinding of the dissolved lutein CPM and $CaCl_2$ mixture, the $CaCl_2$ salt particles distribute evenly through the dissolved paste to form a coating layer around single and/or multiple lutein-ester nano-and meso-capsules to finally yield a dry powder of lutein capsules encapsulated with the $CaCl_2$ coating layer.

EXAMPLE 10

Suspension Preparation Using Lutein-ester/$CaCl_2$ Powder

The powder sample prepared according to example 9 was dissolved in cold deionized water (2° C.) to yield a homogeneous solution of lutein-ester capsules.

EXAMPLE 11

Friable Powder Preparation Using Lutein-ester Capsules and Corn Starch

Three grams of corn starch was added to 1.5 g of lutein-ester capsular matrix prepared according to example 1 after dissolving the capsular matrix at 40° C. The dissolved capsular matrix-starch mixture was grounded to yield dry powder of starch-coated lutein capsules. The resultant lutein-ester/starch powder contained 0.5 percent by weight lutein-ester and resembled the one described in example 9.

EXAMPLE 12

Figure 5:
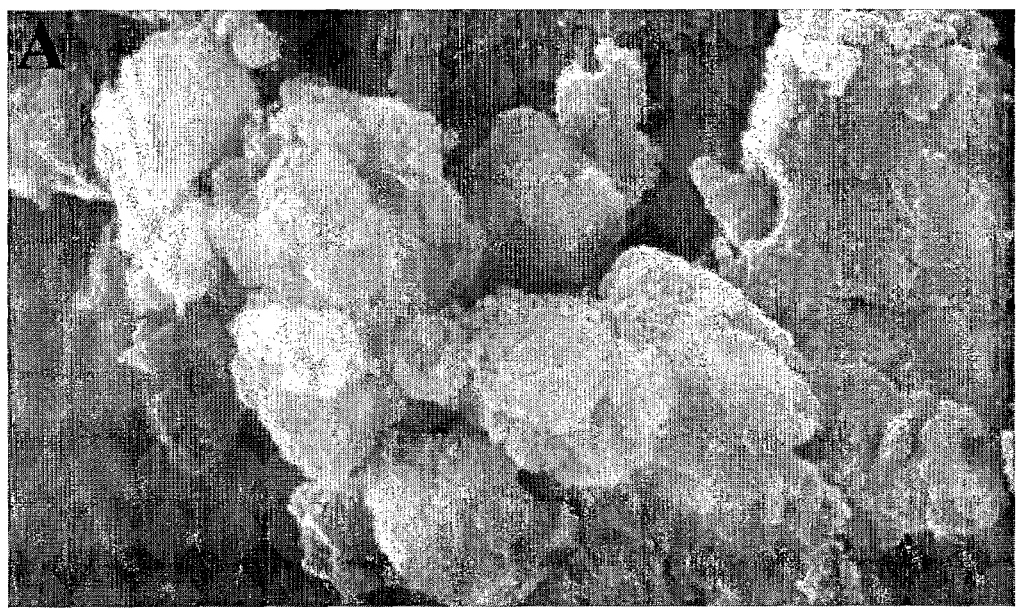
FIG. 5 is a scanning electron micrograph of mesocapsule aggregates coated with SiO2 nanoparticles.

Friable Powder Preparation Using Lutein-ester Capsular Matrix and Colloidal Silica One milliliter of colloidal silica (10-25 nm size) suspension was added to 1 g of the lutein-ester CPM prepared according to example 1. The sample was then placed under vacuum at 70° C. for 1-hr until dried, and then grounded until a dry powder of silicacoated lutein-ester capsules was obtained. FIG. 5 illustrates a scanning electron micrograph of aggregates of lutein-ester nano-and meso-capsules coated with a layer of small silica nanoparticle.

Figure 6:
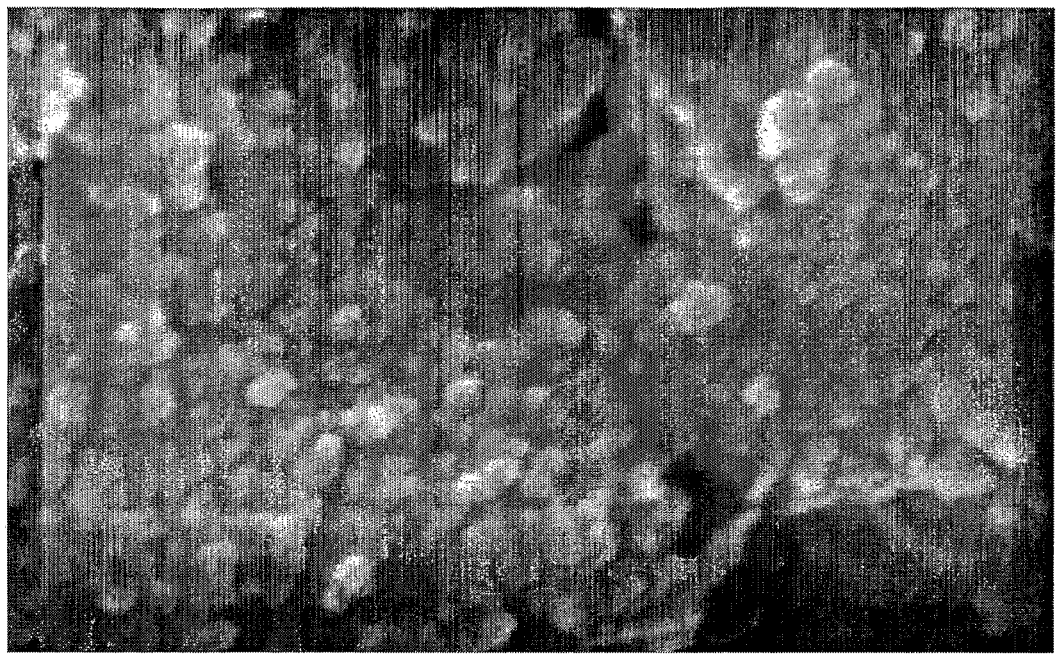
FIG. 6 is a scanning electron micrograph showing the $SiO_2$ nanoparticles that are coating the surface of mesocapsule aggregates shown in FIG. 5.

These colloidal silica contribute to the formation of the dry powder in a similar manner as the $CaCl_2$ salt discussed in example 9. Heating the lutein capsular matrix reduces the capsular matrix from paste into suspension of nano-and meso-capsules. Small silica nanoparticles (FIG. 6) present in the suspension distribute through the suspension and form a coating layer around single and/or multiple lutein-ester nano-and meso-capsules aggregates to finally yield a dry powder of lutein capsules encapsulated within the silica coating layer. The presence of the aggregates seen in FIG. 5 indicates that lutein-ester nano-and meso-capsules are contained within the powder.

EXAMPLE 13

Suspension Preparation Using Lutein-ester/Colloidal Silica Powder

Fifty milligrams of the powder prepared in example 12 was added to 5 ml of deionized water to yield a homogeneous suspension of silica-coated-lutein-ester nano-and meso-capsules. This suspension resembled the suspension discussed in example 10. The ability to dissolve the resultant powder in water indicates that the powder material contains lutein-ester nano-and meso-capsules coated with the charged silica nanoparticles. The orange color of the resultant suspension further confirmed that lutein-ester is contained in the powder material.

Although the present invention and its advantages have been described in detail, it should be understood that various changes, substitutions, and alterations may be made herein without departing from the spirit and scope of the invention as defined by the appended claims.

What is claimed is:

1. A method of encapsulation comprising:
   a) admixing a hydrophobic compound in an organic solvent to form a mixture;
   b) admixing an anionic polyelectrolyte and a cationic polyelectrolyte with the mixture to form a suspension of encapsulated hydrophobic particles;
   c) quiescently cooling the suspension so as to cause self-crosslinking of the encapsulated hydrophobic particles to form a capsular matrix,
   wherein the capsular matrix is not an agglomeration of capsules.

2. The method of claim 1, wherein step (a) comprises admixing an amount of said hydrophobic compound in said organic solvent at a concentration greater than the saturation point of said organic solvent so as to form a mixture comprising a solution of the hydrophobic compound and a suspension of undissolved hydrophobic particles.

3. The method of claim 1 wherein said mixture is a solution.

4. The method of claim 1 wherein said mixture is an emulsion.

5. The method of claim 1 wherein said mixture is a suspension.

6. The method of claim 1 wherein step (b) comprises admixing the anionic polyelectrolyte before the cationic polyelectrolyte.

7. The method of claim 1 wherein step (b) comprises admixing the cationic polyelectrolyte before the anionic polyelectrolyte.

8. The method of claim 1 wherein step (b) comprises admixing the cationic polyelectrolyte and the anionic polyelectrolyte simultaneously.

9. The method of claim 1 wherein step (b) comprises admixing the cationic polyelectrolyte and the anionic polyelectrolyte at a cationic polyelectrolyte to anionic polyelectrolyte weight ratio of at least 2:1.

10. The method of claim 1 wherein step (a) comprises dispersing the hydrophobic compound at a temperature ranging from 40° C. to 80° C.

11. The method of claim 1 wherein step (b) comprises admixing the anionic polyelectrolyte and the cationic polyelectrolyte at a temperature ranging from 40° C. to 60° C.

12. The method of claim 1 wherein step (c) comprises cooling the mixture to a temperature ranging from 20° C. to 30° C.

13. The method of claim 1 wherein step (c) comprises cooling the mixture at a pH ranging from 5 to 6.

14. The method of claim 1 further comprising adjusting the pH of the mixture after step (b).

15. The method of claim 1 further comprising dissolving the capsular matrix in water at a temperature ranging from 40° C. to 60° C. to form a suspension of capsules having an average diameter ranging from 1 nm to 1000 nm.

16. The method of claim 1 wherein the cationic polyelectrolyte is a gelatin.

17. The method of claim 1 wherein the cationic polyelectrolyte comprises chitosan, whey protein, albumin, beta-lactoglobulin, potato protein, faba bean legumin, soybean protein, or combinations thereof.

18. The method of claim 1 wherein the anionic polyelectrolyte is gum arabic.

19. The method of claim 1 wherein the anionic polyelectrolyte comprises any anionic polysaccharide, alginate, pectin, agar, carrageenan, or combinations thereof.

20. The method of claim 1 wherein the hydrophobic compound comprises a carotenoid.

21. The method of claim 20 wherein the carotenoid comprises lutein, antheraxanthin, astaxanthin, canthaxanthin, a-carotene, beta-carotene, cryptoxanthin, diatoxanthin, fucoxanthin, fucoxanthinol, lactucaxanthin, lycopene, neoxanthin, neurosporene, peridinin, phytoene, rhodopin, siphonaxanthin, spheroidene, spirilloxanthin, uriolide, uriolide acetate, violaxanthin, zeaxanthin, or combinations thereof.

22. The method of claim 1 wherein the hydrophobic compound is selected from the group consisting of phytosterols and coenzymes Q.

23. The method of claim 1 wherein the encapsulated hydrophobic particles have an average diameter ranging from about 1 nm to about 1000 nm.

24. The method of claim 1 wherein the organic solvent comprises an alcohol.

25. The method of claim 1 wherein the hydrophobic compound is an oil.

26. The method of claim 1, further comprising adding a binder to the capsular matrix to dissolve the capsular matrix.

27. The method of claim 25, further comprising grinding the capsular matrix into a powder.

28. The method of claim 26 wherein the binder is a salt.

29. The method of claim 28 wherein the binder comprises calcium chloride, sodium chloride, sodium bicarbonate, sodium sulfate, calcium carbonate, magnesium sulfate, starch or combinations thereof.

30. The method of claim 27 wherein said powder is soluble in warm water.

31. The method of claim 27 wherein said powder is soluble in cold water.

32. A capsular matrix comprising:
a self-crosslinked network of capsules encapsulating a plurality of hydrophobic particles, wherein each capsule comprises a cationic polyelectrolyte and an anionic polyelectrolyte and wherein the capsular matrix is not an agglomeration of capsules.

33. The capsular matrix of claim 32 wherein said self-crosslinked network of capsules is water-soluble.

34. The capsular matrix of claim 32 wherein said cationic polyelectrolyte comprises gelatin.

35. The capsular matrix of claim 32 wherein said anionic polyelectrolyte comprises gum arabic.

* * * * *